United States Patent
Zhang et al.

(10) Patent No.: US 9,728,806 B2
(45) Date of Patent: Aug. 8, 2017

(54) FUNCTIONALIZED CHOLINE CHLORIDE IONIC LIQUID, PREPARATION METHOD THEREOF AND USE IN ELECTROCHEMICAL ENERGY STORAGE DEVICE

(71) Applicants: GUANGZHOU INSTITUTE OF ENERGY CONVERSION, CHINESE ACADEMY OF SCIENCES, Tianhe Guangzhou, Guangdone (CN); Lingzhi Zhang, Tianhe Guangzhou (CN); Tianqiao Yong, Tianhe Guangzhou (CN)

(72) Inventors: Lingzhi Zhang, Tianhe Guangzhou (CN); Tianqiao Yong, Tianhe Guangzhou (CN)

(73) Assignee: Guangzhou Institute of Energy Conversion, Chinese Academy Of Sciences, Tianhe Guangzhou, Guangdong (CN)

( * ) Notice: Subject to any disclaimer, the term of this patent is extended or adjusted under 35 U.S.C. 154(b) by 58 days.

(21) Appl. No.: 14/648,859

(22) PCT Filed: Sep. 4, 2013

(86) PCT No.: PCT/CN2013/082892
§ 371 (c)(1),
(2) Date: Jun. 1, 2015

(87) PCT Pub. No.: WO2014/101460
PCT Pub. Date: Jul. 3, 2014

(65) Prior Publication Data
US 2015/0303511 A1   Oct. 22, 2015

(30) Foreign Application Priority Data

Dec. 28, 2012  (CN) .......................... 2012 1 0585742

(51) Int. Cl.
*C07C 253/30* (2006.01)
*C07F 7/18* (2006.01)
(Continued)

(52) U.S. Cl.
CPC ....... *H01M 10/0525* (2013.01); *C07C 213/06* (2013.01); *C07C 215/40* (2013.01); *C07C 217/08* (2013.01); *C07C 253/30* (2013.01); *C07C 255/16* (2013.01); *C07C 311/00* (2013.01); *C07C 311/48* (2013.01); *C07F 5/022* (2013.01); *C07F 7/10* (2013.01); *C07F 7/188* (2013.01); *C07F 7/1852* (2013.01); *H01G 11/62* (2013.01); *H01M 10/0567* (2013.01);
(Continued)

(58) Field of Classification Search
CPC ... H01M 1/525; H01M 10/525; C07C 311/00; C07C 253/30; C07F 7/18; C07F 5/02
USPC ......................................................... 556/413
See application file for complete search history.

(56) References Cited

FOREIGN PATENT DOCUMENTS

| CN | 101390245 A | 3/2009 |
|---|---|---|
| CN | 102372732 A | 3/2012 |

(Continued)

OTHER PUBLICATIONS

Welton, Chem. Rev. 1999, 99, 2071-2083.*
Zablotskaya et al., Applied Organomet. Chem. (2006), 20(11), 721-728.*
(Continued)

*Primary Examiner* — Sudhakar Katakam
*Assistant Examiner* — Kofi Adzamli
(74) *Attorney, Agent, or Firm* — Pearne & Gordon LLP

(57) ABSTRACT

The present invention discloses a process for preparing a functionalized choline chloride ionic liquid as defined in formula (I), and thereof use in an electrochemical energy storage device, as an electrolyte solution or an additive for a lithium ion battery and a supercapacitor. The ionic liquid electrolyte material has better biocompatibility, flame retardance, high ionic conductivity, low viscosity, and wide electrochemical window.

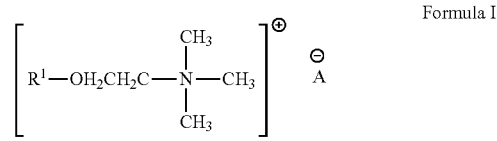

Formula I wherein $R^1$ is selected from the group consisting of: $(CH_2=CH-(CH_2)_n)-$, $CN(CH_2)_n-$, or $R^2{}_3Si-$; $R^2$ is selected from $CH_3-(CH_2)_m-$, n is an integer selected from 1 to 3, m is an integer selected from 0 to 2; or one of $R^2$ is $(CH_3)_3Si-O-$. Anion A in Formula I is selected from the group consisting of: $Cl^-$, $Br^-$, $I^-$, $BF_4^-$, $NO_3^-$, $SO_4^{2-}$, $CF_3COO^-$, $CF_3SO_3^-$, $(CF_3SO_2)_2N^-$, $PF_6^-$, $BF_2C_2O_4^-$, or $B(C_2O_4)_2^-$.

5 Claims, 5 Drawing Sheets

(51) Int. Cl.
*H01M 10/0525* (2010.01)
*C07C 213/06* (2006.01)
*C07C 215/40* (2006.01)
*C07C 217/08* (2006.01)
*H01G 11/62* (2013.01)
*H01M 10/0567* (2010.01)
*C07C 255/16* (2006.01)
*C07C 311/00* (2006.01)
*C07F 5/02* (2006.01)
*C07C 311/48* (2006.01)
*C07F 7/10* (2006.01)
*H01G 11/64* (2013.01)
*H01G 11/04* (2013.01)
*H01M 10/0569* (2010.01)

(52) U.S. Cl.
CPC .............. *H01G 11/04* (2013.01); *H01G 11/64* (2013.01); *H01M 10/0569* (2013.01); *H01M 2300/0025* (2013.01); *Y02E 60/13* (2013.01)

(56) References Cited

FOREIGN PATENT DOCUMENTS

| | | |
|---|---|---|
| CN | 103113242 A | 5/2013 |
| EP | 1724290 A1 | 11/2006 |

OTHER PUBLICATIONS

Rezaei et al., J Solid State Electrochem (2008) 12:1663-1671.*
International Search Report for PCT/CN2013/082892 Dec. 12, 2013.

* cited by examiner

FUNCTIONALIZED CHOLINE CHLORIDE IONIC LIQUID, PREPARATION METHOD THEREOF AND USE IN ELECTROCHEMICAL ENERGY STORAGE DEVICE

This application is a National Stage application of PCT international application PCT/CN2013/082892, filed on Sep. 4, 2013 which claims the priority of Chinese Patent Application No. 201210585742.6 entitled "FUNCTIONALIZED CHOLINE CHLORIDE IONIC LIQUID, PREPARATION METHOD THEREOF AND USE THEREOF IN ELECTROCHEMICAL ENERGY STORAGE DEVICE", filed with the Chinese Patent Office on Dec. 28, 2012, both of which are incorporated herein by reference in their entirety.

TECHNICAL FIELD

The present invention relates to the technical field of chemistry, and in particular, to a functionalized choline chloride room-temperature ionic liquid material, a preparation method and thereof use as an electrolyte material or additive in an electrochemical energy storage device.

BACKGROUND

At present, electrolyte materials used in the lithium ion battery industry are mainly multi-solvent systems of cyclic carbonates and linear carbonates compounds, and $LiPF_6$ lithium salts. The operating mode of the electrolyte system is still exposed to safety risks from technical perspective, which is mainly due to the high volatility and inflammability of the carbonates electrolyte materials. In the application field of hybrid electric vehicles and all-electric vehicles with high requirements for high safety, large capacity, and high rate discharge, the safety issue is an important factor restricting the application of these materials. Therefore, a new generation of safe, effective, and environmentally-friendly organic electrolyte materials are being proactively developed both in China and abroad.

A substance, in the form of liquid at or near room temperature, composed of ions is referred to as the room-temperature ionic liquid, room-temperature molten salt, organic ionic liquid or the like, which, however, tends to be called as ionic liquid. Since such ionic liquid has low volatility and low flammability, better thermal stability, good chemical and electrochemical stability, the ionic liquid gains wide application prospect in such fields as green chemistry, industrial catalysis, industrial solvents or the like. Due to such characteristics as high safety and high electrochemical stability, researches have been proactively conducted in terms of using ionic liquid as an electrolyte solution of a lithium ion battery.

The ionic liquid electrolyte materials for use in the lithium ion batteries can be categorized into two types: one is a molten lithium salt in the form of ionic liquid, and the other is a molten lithium salt in the form of ionic liquid added with a corresponding additive. The first generation of ionic liquid is an organic molten salt with $AlCl_4$ as anions. Such ionic liquid is apt to be hydrolyzed, and reacted with water to give HCl. Therefore, no further study is conducted for the application of the first generation of ionic liquid in the lithium ion batteries. The second generation of ionic liquid is an organic room-temperature molten salt having the imidazole cations as the positive ions and fluorinated inorganic or organic anions as the negative ions. Such ionic liquid exhibits poor electrochemical reduction stability, and thus is not considered having commercial application prospects in the high performance batteries. The third generation of ionic liquid employs the non-imidazoles cations and fluorinated inorganic or organic anions. At present, the most suitable ionic liquid for the lithium ion batteries is N,N-dialkyl piperidine (Patent JP2006260952). However, these ionic liquids cause a greatly reduction of the output power of the lithium ion batteries, because these ionic liquids having high chemical stability have higher viscosity, which compared with the traditional carbonates electrolyte, causes a significant reduction of the conduction velocity of the lithium ions (O. Borodin et. al. J. of Physical Chemistry B, 2006, 10(34), pp. 16879-16886). Compared with the traditional carbonates-based electrolyte lithium ion batteries, the ionic liquid-matrix electrolyte lithium ion batteries still have low output power and small charge capacity. Lee et al. (Electrochem. Comm. 8 (2006) 460) have reported that using the imidazoles ionic liquid with an ester radical on the N atom as the electrolyte of the lithium ion battery improves the conductivity and diffusion velocity of the lithium ions. However, these imidazoles ionic liquids are poor in terms of electrochemical stability. R. West et al. have reported in the U.S. Pat. No. 7,679,884B2 and US2009088583-A1 that silicon-based quaternary phosphonium and silicon-based quaternary ammonium ionic liquids. These ionic liquids exhibit improved electrochemical stability but still have high viscosity.

The choline chloride plays an important role in the cells function, and biosynthesis and degradation of the choline chloride control life activities of the cells. The choline chloride has excellent biocompatibility and is biodegradable. In addition, the choline chloride, as a feed additive or the like, can be industrially manufactured and is thus a very cheap raw material. Further, choline hydroxide has been used as a basic catalyst for the Aldol condensation reaction. The choline derivatives having low melting point are the focus of a variety of researches. Some choline analogs have been successfully synthesized [Pernak, Chemistry—A European Journal, 2007, 13(24), pp. 6817-6827]. [$Me_3NC_2H_4Y$][Cl] (Y=OH, Cl, OC(O)Me, OC(O)Ph) and $MCl_2$ (M=Zn, Sn) is a viscous liquid which is conductive around room temperature, and typically used for electro-deposition. However, choline chloride-based ionic liquid has not been used as an electrolyte or an additive for the lithium ion battery.

SUMMARY

One objective of the present invention is to provide a novel functionalized choline chloride room-temperature ionic liquid.

Another objective of the present invention is to provide the use of the above mentioned functionalized choline chloride room-temperature ionic liquid in an electrochemical energy storage device.

The present invention is achieved by the following technical solutions:

A functionalized choline chloride room-temperature ionic liquid, wherein a cation chemical structural formula thereof is based on the functionalized choline chloride room-temperature ionic liquid having overall chemical structural as formula I:

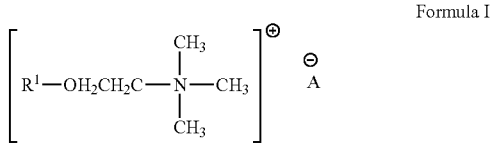

Formula I wherein $R^1$ is selected from the group consisting of: $(CH_2=CH-(CH_2)_n)-$, $CN(CH_2)_n-$, or $R^2_3Si-$; $R^2$ is selected from $CH_3-(CH_2)_m-$; n is an integer selected from 1 to 3, m is an integer selected from 0 to 2; or one of $R^2$ is $(CH_3)_3Si-O-$.

Anion A is selected from the group consisting of: $Cl^-$, $Br^-$, $I^-$, $BF_4^-$, $NO_3^-$, $SO_4^{2-}$, $CF_3COO^-$, $CF_3SO_3^-$, $(CF_3SO_2)_2N^-$, $PF_6^-$, $BF_2C_2O_4^-$, or $B(C_2O_4)_2^-$.

The compound of Formula I may be prepared by Method I and Method II. The methods are detailed as follows:

Method I: Under the condition of cooling in ice bath, the choline chloride is reacted with an equi-molar amount of sodium hydroxide in acetonitrile solvent at room temperature for 20 minutes, and followed by adding drop-wise 1.1 times molar amount of $R^1$—X halogenated alkane thereto for reaction under reflux for 8 hours, or the choline chloride is reacted with an equi-molar amount of organosilicon reagent (for example, hexamethyl disilazane, pentamethyl chlorodisiloxane, and trimethylchlorosilane) under reflux for 16 hours. After the reaction is completed, the resulting reaction product is filtered to remove solid and treated via rotary evaporation to remove solvent, followed by recrystallization using dichloromethane and diethyl ether as solvent to obtain the $R^1$— and $R^2_3Si$—functionalized choline chloride ionic liquid. The functionalized choline chloride ionic liquid and an equi-molar amount of alkali metal or alkaline earth metal salt MA (wherein anion A is $BF_4^-$, $NO_3^-$, $SO_4^{2-}$, $CF_3COO^-$, $CF_3SO_3^-$, $(CF_3SO_2)_2N^-$, $PF_6^-$, $BF_2C_2O_4^-$, or $B(C_2O_4)_2^-$) is dissolved in water or other solvents for anion exchange, and allowed to react under stirring for 4 to 6 hours. Subsequently, the product obtained from the ion exchange is extracted by using dichloromethane, removed the solvents, and dried to obtain the target ionic liquid.

The reaction route of Method I is as follows:

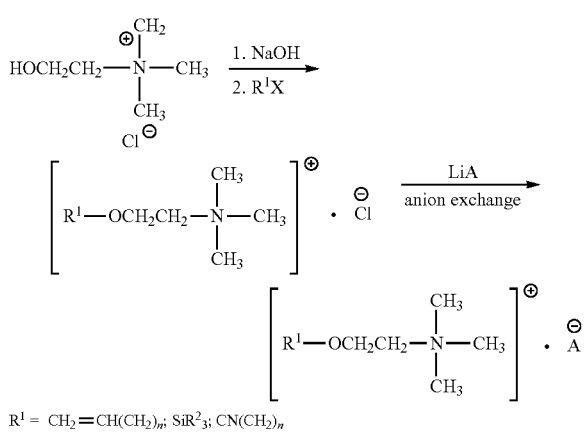

$R^1 = CH_2=CH(CH_2)_n$; $SiR^2_3$; $CN(CH_2)_n$

Method II: In case that $R^1$ is $R^2_3Si-$, the choline chloride and an equi-molar amount of alkali metal or alkaline earth metal salt MA (wherein anion A is $BF_4^-$, $NO_3^-$, $SO_4^{2-}$, $CF_3COO^-$, $CF_3SO_3^-$, $(CF_3SO_2)_2N^-$, $PF_6^-$, $BF_2C_2O_4^-$, or $B(C_2O_4)_2^-$) are dissolved in water or other solvents at room temperature for anion exchange, and the reaction is stirred for 4 to 6 hours. The resulting reaction product is extracted with dichloromethane or other solvents, and then treated to remove the solvent to obtain a choline chloride ionic liquid obtained from the anion exchange. In the second reaction step, the choline chloride ionic liquid obtained from the anion exchange is reacted with a corresponding organosilicon reagent (for example, hexamethyl disilazane, pentamethyl chlorodisiloxane, and trimethylchlorosilane) under reflux for 16 hours, and concentrated under vacuum to remove residual low boiling-point substances to obtain the target ionic liquid.

The reaction route of Method II is as follows:

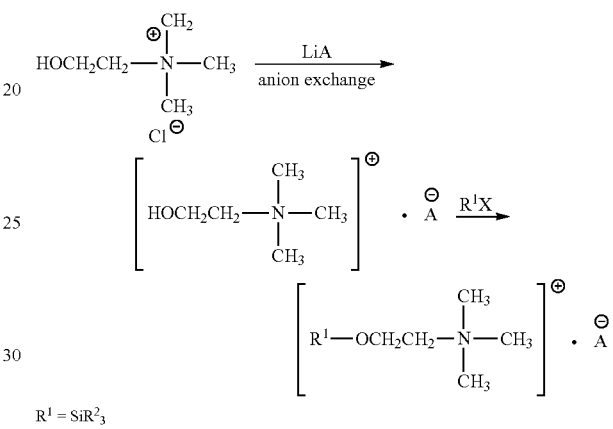

$R^1 = SiR^2_3$

Still another objective of the present invention is to provide the use of the functionalized choline chloride ionic liquid as an electrolyte material or additive in an electrochemical energy storage device.

The room-temperature ionic liquid electrolyte material may be used as a quaternary ammonium salt-type ionic liquid electrolyte material, which may be applied as an electrolyte material or an additive for lithium ion batteries. The anode of the lithium ion battery may be one selected from the group consisting of graphite, lithium titanate, and nano-silicon; and the cathode of the lithium ion battery may be one selected from the group consisting of $LiCoO_2$, lithium iron phosphate, $LiNi_{1/3}Mn_{1/3}Co_{1/3}O_2$,/$LiNi_{0.5}Mn_{0.5}O_2$, and $LiMnO_2$.

The room-temperature ionic liquid electrolyte material may be used as a quaternary ammonium salt-type ionic liquid electrolyte material, which may be applied as an electrolyte material or an additive for electrochemical supercapacitors. Electrodes of the electrochemical supercapacitor may be selected from the group consisting of active carbon, metal oxide, and conductive polymer.

The present invention achieves the following beneficial effects: compared with the prior art, the ionic liquid electrolyte material has better biocompatibility, flame retardance, high ionic conductivity, low viscosity, and wide electrochemical window.

DETAILED DESCRIPTION

Figure 1:
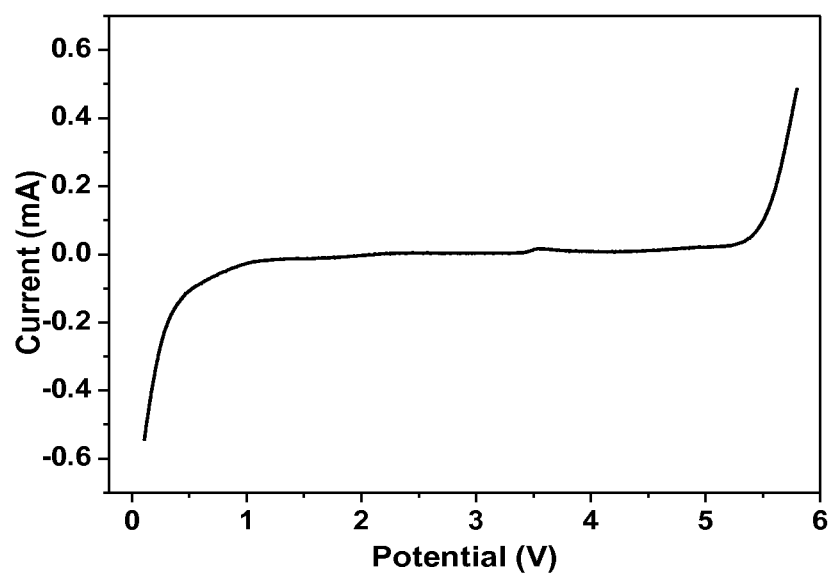
FIG. 1 is a linear sweep voltammetry plot of 2-allyloxy-ethyl trimethyl ammonium bis(trifluoromethylsulfonyl)imide.

The present invention is further described with reference to specific embodiments.

However, such embodiments construe no limitation to the protection scope of the present invention.

Example 1: Synthesis of 2-allyloxyethyl trimethyl ammonium chloride salt

Under the condition of cooling in ice bath, 0.5 mol of choline chloride was reacted with an equi-molar amount of sodium hydroxide in an acetonitrile solvent at room temperature for 20 minutes, and then 0.55 mol of allyl bromide was added drop-wise thereto. The resulting reaction mixture was reacted under reflux for 8 hours. After the reaction is completed, the resulting reaction product was filtered to remove the solid, and treated via rotary evaporation to remove solvent. The residue was recrystallized from the solvents of dichloromethane and diethyl ether to obtain 2-allyloxyethyl trimethyl ammonium chloride salt: $^1$H NMR (CDCl$_3$): σ 3.47 (m, 9H, +N(CH$_3$)$_3$), 3.90, 3.94 (dd, 4H, OCH$_2$CH$_2$O), 4.02 (m, 2H, CH$_2$=CH—CH$_2$—O), 5.23 (ddq, 2H, CH$_2$=CH—CH$_2$—O), 5.84 (ddt, 1H, CH$_2$=CH—CH$_2$—O); $^{13}$C NMR (CDCl$_3$): σ 54.61, 63.98, 65.68, 72.21, 118.43, 133.27.

Example 2: Synthesis of 2-allyloxyethyl trimethyl ammonium bis(trifluoromethylsulfonyl)imide salt 0.4 mol of 2-allyloxyethyl trimethyl ammonium chloride salt (the product obtained in Example 1) and an equi-molar amount of lithium bis(trifluoromethylsulfonyl)imide were dissolved in water for anion exchange, and mechanically stirred for 4 to 6 hours. Subsequently, the product obtained from the anion exchange was extracted by using the dichloromethane solvent, concentrated to remove the solvent. The residue was dried to obtain the target 2-allyloxyethyl trimethyl ammonium bis(trifluoromethylsulfonyl)imide salt ionic liquid: $^1$H NMR (CDCl$_3$): σ 3.19 (m, 9H, +N(CH$_3$)$_3$), 3.58, 3.86 (m, 4H, OCH$_2$CH$_2$O), 4.05 (m, 2H, CH$_2$=CH—CH$_2$—O), 5.28 (ddq, 2H, CH$_2$=CH—CH$_2$—O), 5.85 (m, 1H, CH$_2$=CH—CH$_2$—O); $^{13}$C NMR (CDCl$_3$): σ 54.65, 63.50, 66.20, 72.31, 118.70, 132.97.

Example 3: Synthesis of choline bis(trifluoromethylsulfonyl)imide salt

At room temperature, 0.5 mol of choline chloride and an equi-molar amount of lithium bis(trifluoromethylsulfonyl) imide were dissolved in water for ion exchange, and mechanically stirred for 4 to 6 hours. The resulting reaction product was then extracted with dichloromethane, and then treated to remove the solvent to yield the choline bis (trifluoromethylsulfonyl)imide salt obtained from the anion exchange: $^1$H NMR (300 MHz, CDCl$_3$): δ 6 3.16 (s, 9H, +N(CH$_3$)$_3$), 3.40 (s, 1H, OH), 3.45 (s, 2H, CH$_2$O), 4.03 (s, 2H, CH$_2$N+); $^{13}$C NMR (300 MHz, CDCl$_3$): 54.06, 56.21, 67.66, 119.75.

Example 4: Synthesis of 2-trimethylsiloxyethyl trimethyl ammonium bis(trifluoromethylsulfonyl)imide salt 0.4 mol of hexamethyl disilazane was added drop-wise into 0.4 mol of choline bis(trifluoromethylsulfonyl)imide salt (the product obtained in Example 3) and reacted under reflux for 16 hours. The resulting reaction product was evaporated under vacuum to remove residual low boiling-point substances to obtain the target 2-trimethylsiloxyethyl trimethyl ammonium bis(trifluoromethylsulfonyl)imide salt ionic liquid: $^1$H NMR (300 MHz, CDCl$_3$): δ 0.16 (s, 9H, Si(CH$_3$)$_3$), 3.22 (s, 9H, +N(CH$_3$)$_3$), 3.50 (s, 2H, CH$_2$O), 4.00 (s, 2H, CH$_2$N+); $^{13}$C NMR (75 MHz, CDCl$_3$): −1.04, 54.55, 56.81, 67.86, 119.87.

Example 5: Synthesis of 2-allyloxyethyl trimethyl ammonium bis(oxalate)borate salt 2-allyloxyethyl trimethyl ammonium bis(oxalate)borate salt was synthesized by using the process similar to that disclosed in Example 2. 0.4 mol of 2-allyloxyethyl trimethyl ammonium chloride salt (the product obtained in Example 1) and an equi-molar amount of lithium bis(oxalate)borate were dissolved in water for anion exchange, and the resulting solution was mechanically stirred for 4 to 6 hours. Subsequently, the product obtained from the anion exchange was extracted by using dichloromethane, removed the solvent. The residue was dried to obtain the target 2-allyloxyethyl trimethyl ammonium bis(oxalate)borate salt ionic liquid: $^1$H NMR (CDCl$_3$): σ 3.44 (m, 9H, +N(CH$_3$)$_3$), 3.89, 3.91 (m, 4H, OCH$_2$CH$_2$O), 4.04 (m, 2H, CH$_2$=CH—CH$_2$—O), 5.28 (ddq, 2H, CH$_2$=CH—CH$_2$—O), 5.87 (m, 1H, CH$_2$=CH—CH$_2$—O); $^{13}$C NMR (CDCl$_3$): σ 54.67, 63.63, 66.92, 72.37, 118.85, 132.01, 158.89.

Example 6: Synthesis of 2-allyloxyethyl trimethyl ammonium bis(fluorooxalate)borate salt 2-allyloxyethyl trimethyl ammonium bis(fluorooxalate) borate salt was synthesized by using the process similar to that disclosed in Example 2. 0.4 mol of 2-allyloxyethyl trimethyl ammonium chloride salt (the product obtained in Example 1) and an equi-molar amount of lithium bis(fluorooxalate)borate were dissolved in water for anion exchange, and the resulting solution was mechanically stirred for 4 to 6 hours. Subsequently, the product obtained from the anion exchange was extracted by using the dichloromethane solvent, concentrated to remove the solvent. The residue was dried to obtain the target 2-allyloxyethyl trimethyl ammonium bis(fluorooxalate)borate salt: $^1$H NMR (CDCl$_3$) ionic liquid: σ 3.38 (m, 9H, +N(CH$_3$)$_3$), 3.80, 3.89 (m, 4H, OCH$_2$CH$_2$O), 4.03 (m, 2H, CH$_2$=CH—CH$_2$—O), 5.27 (ddq, 2H, CH$_2$=CH—CH$_2$—O), 5.87 (m, 1H, CH$_2$=CH—CH$_2$—O); $^{13}$C NMR (CDCl$_3$): σ 54.64, 63.67, 66.72, 72.22, 118.67, 133.05, 160.28.

Example 7: Synthesis of 2-cyanopropyloxyethyl trimethyl ammonium chloride salt 2-cyanopropyloxyethyl trimethyl ammonium chloride salt was synthesized by using the process similar to that disclosed in Example 1. Under the condition of cooling in ice bath, 0.5 ml of choline chloride was reacted with 0.5 mol of sodium hydroxide in an acetonitrile solvent at room temperature for 20 minutes, and then 0.55 mol of cyanopropyl bromide was added drop-wise thereto. The resulting reaction mixture was reacted under reflux for 8 hours. The resulting reaction product was treated via rotary evaporation to remove solvent. The residue was recrystallized from the solvents of methanol and diethyl ether to obtain 2-cyanopropyloxyethyl trimethyl ammonium chloride salt: $^1$H NMR (CDCl$_3$): σ 3.40 (m, 9H, +N(CH$_3$)$_3$), 3.88, 3.94 (dd, 4H, OCH$_2$CH$_2$O), 3.68 (m, 2H, CNCH$_2$—CH$_2$—O), 2.72 (m, 2H, CN—CH$_2$—CH$_2$—O).

Description of Electrochemical Energy Storage Performance

Example 8: Performance of 2-allyloxyethyl trimethyl ammonium bis(trifluoromethylsulfonyl)imide salt The electrochemical energy storage performance of the functionalized choline chloride room-temperature ionic liquid according to the present invention is described by using 2-allyloxyethyl trimethyl ammonium bis(trifluoromethylsulfonyl)imide salt (the product obtained in Example 2) as an example.

The measurement of the electrochemical window of 2-allyloxyethyl trimethyl ammonium bis(trifluoromethylsulfonyl)imide salt employs a three-electrode glass battery system, wherein Pt wire was used as an operating electrode, Li wire was used as a counter electrode, and the other Li wire was used as a reference electrode. The obtained linear sweep voltammetry plot was as illustrated in FIG. 1, wherein the electrochemical window was 0.5 to 5.2 V, better than that of an imidazoles ionic liquid (which generally has an electrochemical window of 4 V, A. Lewandowski, Journal of Power Sources 194 (2009) 601-609).

Figure 2:
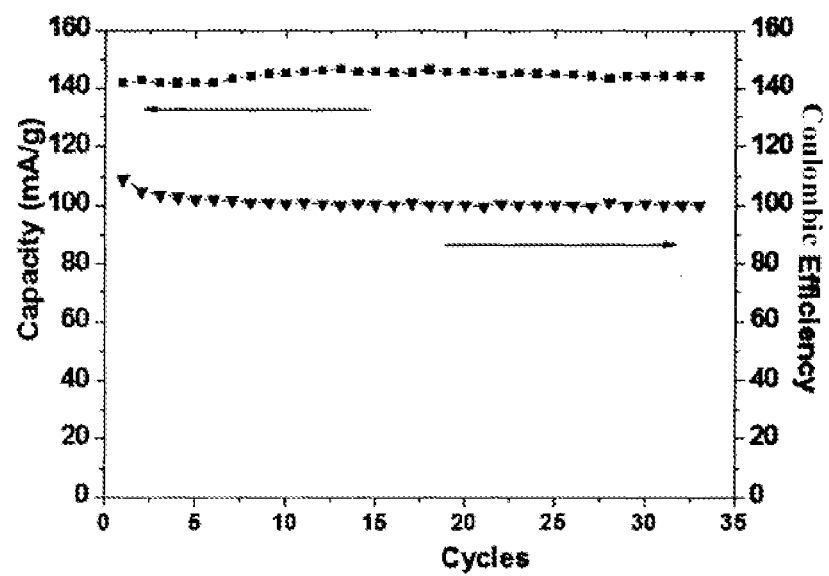
FIG. 2 illustrates cyclic performance of a lithium titanate lithium metal battery in which 0.8 M lithium bis(trifluoromethylsulfonyl)imide in 2-allyloxyethyl trimethyl ammonium bis(trifluoromethylsulfonyl)imide ionic liquid as an electrolyte (■ indicates a specific capacity, and ▼ indicates a Coulombic efficiency)

0.8 M lithium bis(trifluoromethylsulfonyl)imide was added into 2-allyloxyethyl trimethyl ammonium bis(trifluoromethylsulfonyl)imide salt to obtain an electrolyte solution without additive. The cyclic performance of a lithium metal battery using the obtained electrolyte solution and lithium titanate as the cathode was as illustrated in FIG. 2. The circulation was stable and the capacity was maintained at 145 mAh/g, with no attenuation.

Figure 3:
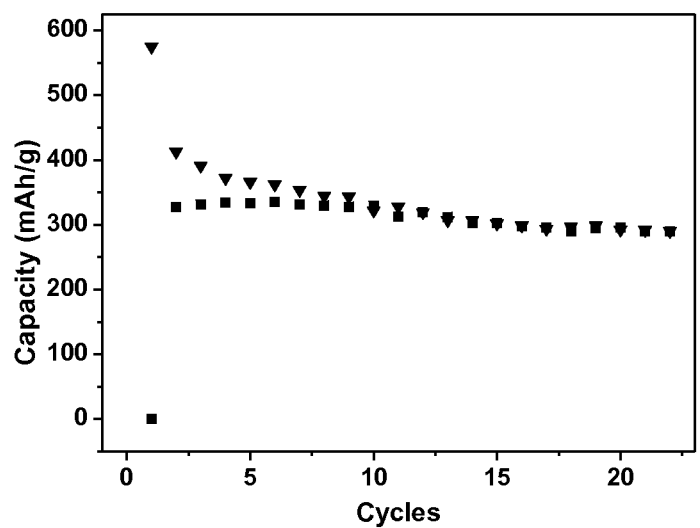
FIG. 3 illustrates cyclic performance of a graphite half-cell in which 0.8 M lithium bis(trifluoromethylsulfonyl) imide in 2-allyloxyethyl trimethyl ammonium bis(trifluoromethylsulfonyl)imide ionic liquid with 10% vinylene carbonate as an additive as an electrolyte (■ indicates a specific discharge capacity, and ▼ indicates a specific charge capacity)

0.8 M lithium bis(trifluoromethylsulfonyl)imide and 10% vinylene carbonate were added into 2-allyloxyethyl trimethyl ammonium bis(trifluoromethylsulfonyl)imide salt to obtain an electrolyte solution having an additive. The cyclic performance of the half-cell using the obtained electrolyte solution and graphite as the cathode is as illustrated in FIG. 3.

Figure 4:
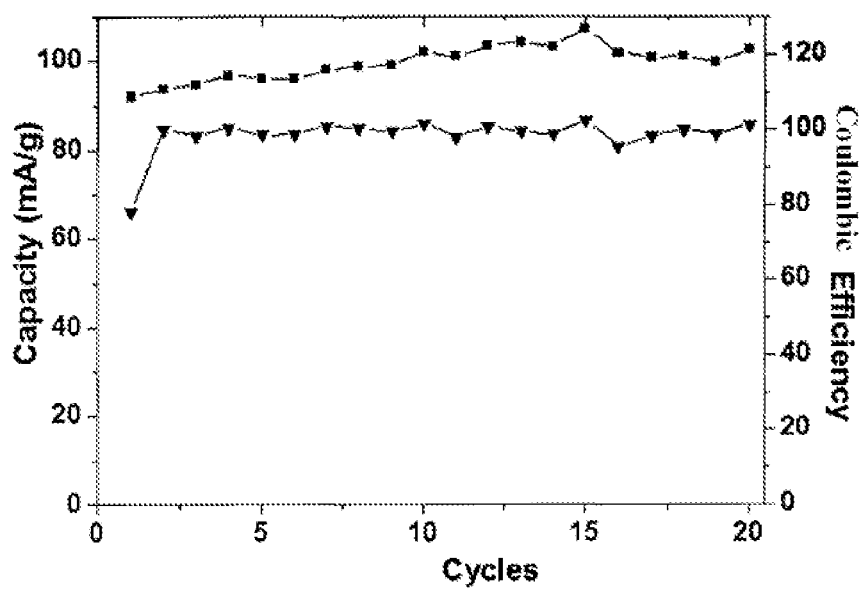
FIG. 4 illustrates cyclic performance of a lithium iron phosphate lithium metal battery in which 0.8 M 2-allyloxyethyl trimethyl ammonium bis(trifluoromethylsulfonyl)imide ionic liquid of bis(trifluoromethylsulfonyl)imide lithium with 10% vinylene carbonate as an additive as an electrolyte (■ indicates a specific capacity, and ▼ indicates a Coulombic efficiency)

0.8 M lithium bis(trifluoromethylsulfonyl)imide and 10% vinylene carbonate were added into 2-allyloxyethyl trimethyl ammonium bis(trifluoromethylsulfonyl)imide salt to obtain an electrolyte solution having an additive. The cyclic performance of a lithium metal battery using the obtained electrolyte solution and lithium iron phosphate as the cathode is as illustrated in FIG. 4.

Example 9: Performance of 2-trimethylsiloxyethyl trimethyl ammonium bis(trifluoromethylsulfonyl)imide salt The electrochemical energy storage performance of the functionalized choline chloride room-temperature ionic liquid according to the present invention is described by using 2-trimethylsiloxyethyl trimethyl ammonium bis(trifluoromethylsulfonyl)imide (the product obtained in Example 4) as an example.

Figure 5:
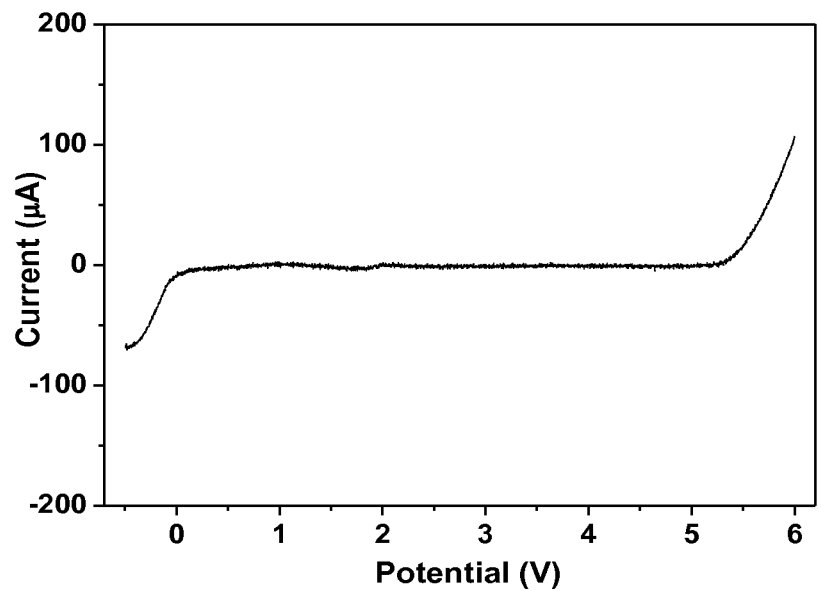
FIG. 5 is a linear sweep voltammetry plot of 2-trimethylsiloxyethyl trimethyl ammonium bis(trifluoromethylsulfonyl)imide.

The measurement of the electrochemical window of 2-trimethylsiloxyethyl trimethyl ammonium bis(trifluoromethylsulfonyl)imide salt employs a three-electrode glass battery system, wherein Pt wire was used as an operating electrode, Li wire was used as a counter electrode, and the other Li wire was used as a reference electrode. The obtained linear sweep voltammetry plot of 2-trimethylsiloxyethyl trimethyl ammonium bis(trifluoromethylsulfonyl)imide was as illustrated in FIG. 5, wherein the electrochemical window thereof was 0 to 5.3 V. The reduction potential of the obtained battery is lower than that of an imidazoles ionic liquid (which is generally 1 V vs. Li/Li$^1$), and the oxidation potential thereof is also higher than that of the imidazoles ionic liquid (which is generally 4 V vs. Li/Li$^1$). In addition, since the reduction potential is 0 V, 2-trimethylsiloxyethyl trimethyl ammonium bis(trifluoromethylsulfonyl)imide room-temperature ionic liquid is applicable to a lithium metal battery and a high-voltage lithium metal battery.

Figure 6:
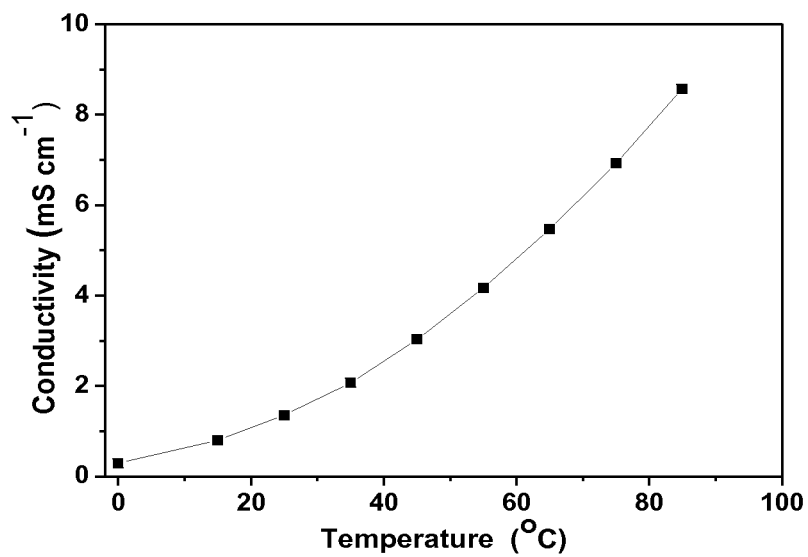
FIG. 6 is a graph illustrating the variation of the conductivity of 2-trimethylsiloxyethyl trimethyl ammonium bis (trifluoromethylsulfonyl)imide with temperature.

The measurement of the conductivity of 2-trimethylsiloxyethyl trimethyl ammonium bis(trifluoromethylsulfonyl) imide salt employs a battery system adopting a glass carbon electrode. Variations of the conductivity with the temperature are as illustrated in FIG. 6.

The performance of an electrochemical supercapacitor formed from the functionalized choline chloride room-temperature ionic liquid according to the present invention is described by using 2-trimethylsiloxyethyl trimethyl ammonium bis(trifluoromethylsulfonyl)imide (the product obtained in Example 4) as an example.

Figure 7:
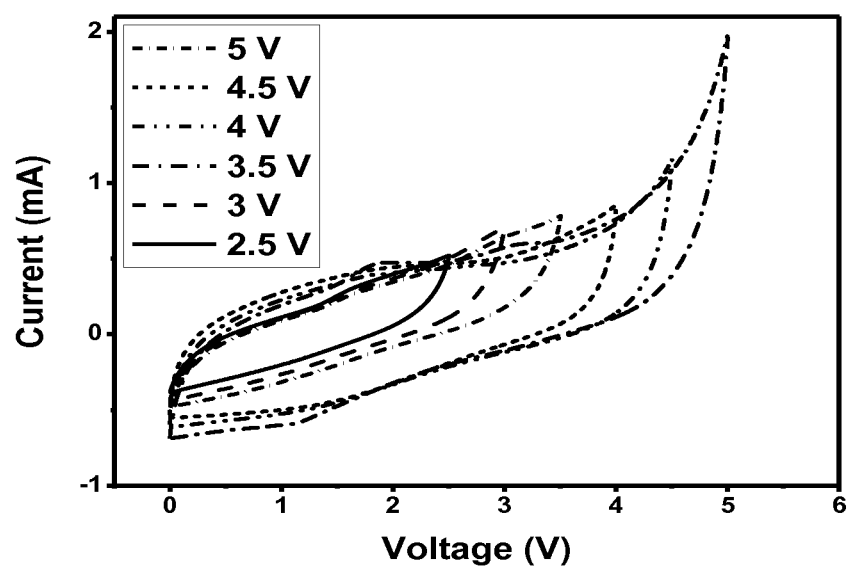
FIG. 7 illustrates cyclic voltammetry performance of a supercapacitor formed from 2-trimethylsiloxyethyl trimethyl ammonium bis(trifluoromethylsulfonyl)imide.

The inventors have investigated cyclic voltammetry performance of a symmetric supercapacitor formed from the active carbon electrode and an electrolyte solution of pure 2-trimethylsiloxyethyl trimethyl ammonium bis(trifluoromethylsulfonyl)imide, under different cut-off voltages (from 1 to 5 V) at a scanning rate of 5 mV/s (as illustrated in FIG. 7). The electrolyte solution falls within the range of 1 to 4 V, and the cyclic voltammetry curve is presented as a symmetric rectangle, which indicates that the active carbon electrode has better reversibility, exhibiting better electric double-layer capacitor features.

Figure 8:
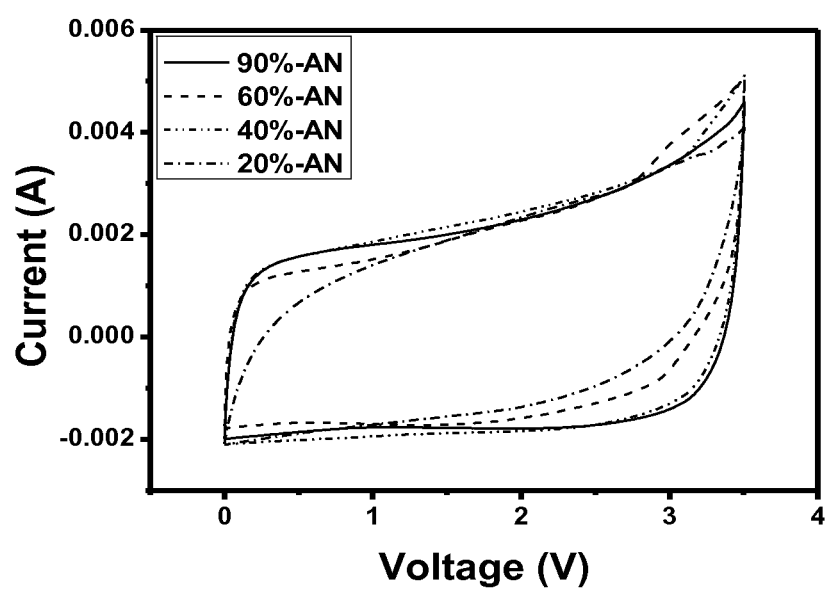
FIG. 8 illustrates cyclic voltammetry performance of a supercapacitor formed from 2-trimethylsiloxyethyl trimethyl ammonium bis(trifluoromethylsulfonyl)imide added with AN.

FIG. 8 illustrates impacts caused by addition of low viscosity AN to the cyclic voltammetry performance of the supercapacitor, wherein with the increase of the adding amount of AN (from 20% to 90%), the cyclic voltammetry curve presents as better rectangles. Therefore, capacitor performance is investigated by using a symmetric supercapacitor formed from the active carbon electrode and an electrolyte solution of the added AN having a volume fraction of 90%/2-trimethylsiloxyethyl trimethyl ammonium bis(trifluoromethylsulfonyl)imide as an electrolyte.

Figure 9:
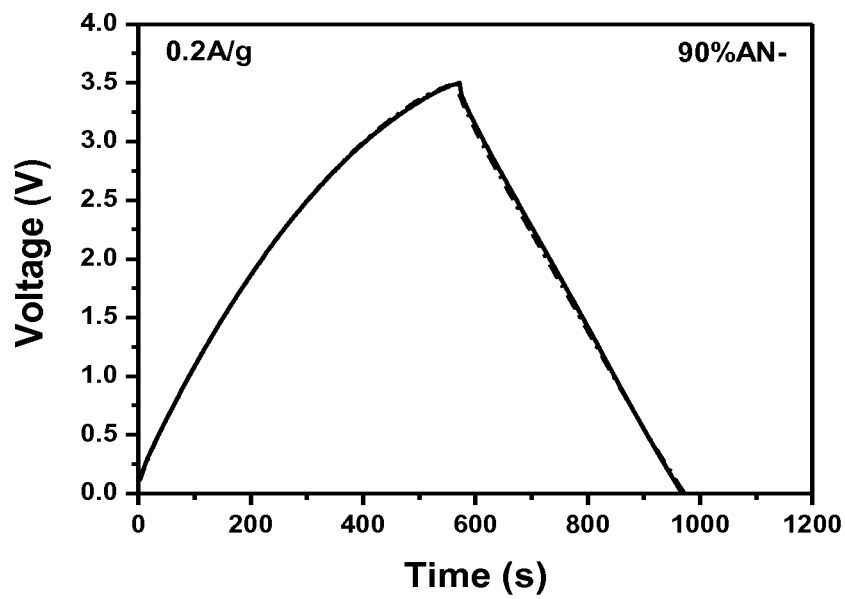
FIG. 9 is a charge and discharge curve of a supercapacitor formed from 2-trimethylsiloxyethyl trimethyl ammonium bis(trifluoromethylsulfonyl)imide added with 90% AN.

FIG. 9 is a constant-current charge/discharge curve of a symmetric supercapacitor formed from the active carbon electrode and an electrolyte solution of 90% AN/2-trimethylsiloxyethyl trimethyl ammonium bis(trifluoromethylsulfonyl)imide as an electrolyte, at a current density of 0.2 A/g. Within a voltage range of from 0 to 3.5 V, the discharge curve of the active carbon electrode displays a linear variation, without obvious gassing phenomenon or damage. The voltage range is far higher than that of the commercial-use tetraethylammonium tetrafluoroborate ($Et_4NBF_4$)/PC electrolyte solution (from 0 to 2.7 V).

Figure 10:
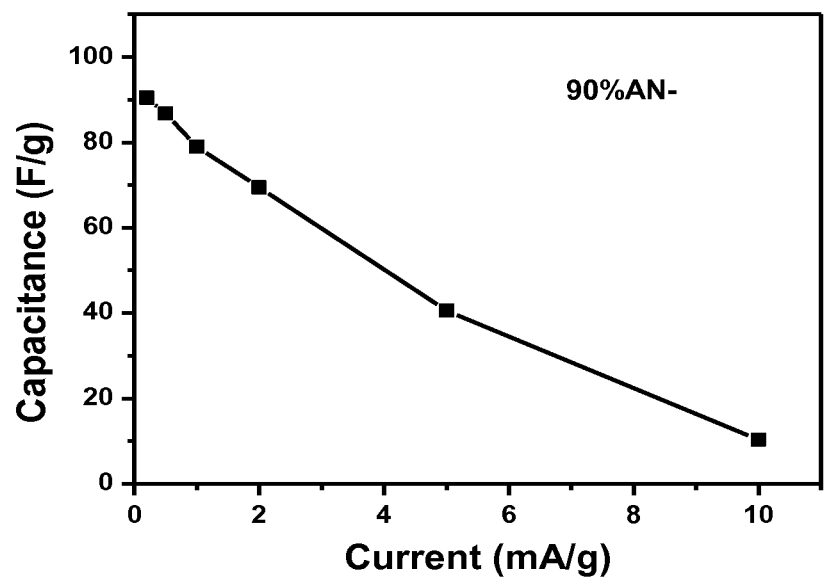
FIG. 10 illustrates great current charge and discharge performance of a supercapacitor formed from 2-trimethylsiloxyethyl trimethyl ammonium bis(trifluoromethylsulfonyl)imide added with 90% AN.

FIG. 10 illustrates a rate capability of a symmetric supercapacitor formed from the active carbon electrode an electrolyte solution of 90% AN/2-trimethylsiloxyethyl trimethyl ammonium bis(trifluoromethylsulfonyl)imide as an electrolyte. When the current density is 0.2 $A·g^{-1}$, the specific capacitance of the active carbon electrode is 90 $F·g^{-1}$; and when the current density increases to 2 $A·g^{-1}$, the specific capacitance still reaches 70 $F·g^{-1}$, exhibiting better charge/discharge performance under great-current.

What is claimed is:

1. A functionalized choline chloride ionic liquid having the following formula I:

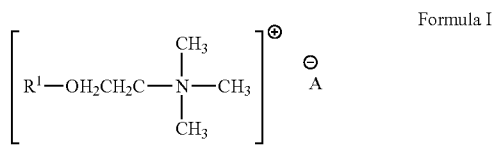

Formula I wherein $R^1$ is $(CH_2=CH-(CH_2)_n)-$, $CN(CH_2)_n-$, or $R^2_3Si-$; $R^2$ is $CH_3-(CH_2)_m-$ or $(CH_3)_3Si-O-$; A is $Cl^-$, $Br^-$, $I^-$, $BF_4^-$, $NO_3^-$, $SO_4^{2-}$, $CF_3COO^-$, $CF_3SO_3^-$, $(CF_3SO_2)_2N^-$, $PF_6^-$, $BF_2C_2O_4^-$, or $B(C_2O_4)_2^-$; n is an integer selected from 1 to 3, m is an integer selected from 0 to 2, and one of $R^2$ is $(CH_3)_3Si-O-$.

2. A process for preparing the functionalized choline chloride ionic liquid according to claim 1, wherein the process comprises the steps of: under a condition of cooling in ice bath, reacting choline chloride with an equi-molar amount of sodium hydroxide in an acetonitrile as solvent at room temperature for 20 minutes, and adding drop-wise 1.1 times molar amount of halogenated alkane thereto, followed by reacting under reflux for 8 hours; or reacting choline chloride with an equi-molar amount of organosilicon reagent under reflux for 16 hours; removing solid by filtering after completion of the reaction, removing solvent by rotary evaporation, and subsequently using dichloromethane and diethyl ether as solvents for recrystallization to obtain the functionalized choline chloride ionic liquid; dissolving the functionalized choline chloride tonic liquid and an equi-molar amount of alkali metal or alkaline earth metal salt in water or other solvents for anion exchange, stirring the reaction for 4 to 6 hours, followed by extracting the product after the ion exchange by using the dichloromethane as a solvent, removing the solvent, and drying to yield the target ion liquid.

3. A process for preparing the functionalized choline chloride room-temperature ionic liquid according to claim 1, wherein the process comprises the steps of: at room temperature, dissolving choline chloride and an equi-molar amount of alkali metal or alkaline earth metal salt in water or other solvents for anion exchange, and reacting under stirring for 4 to 6 hours, followed by using dichloromethane or other solvents for extraction, and removing solvent to obtain a choline chloride ionic liquid obtained from the anion exchange, reacting the choline chloride ionic liquid obtained from the anion exchange with an organosilicon reagent under refluxing for 16 hours, and concentrated under vacuum to remove residual low boiling-point substances to yield the target ionic liquid.

4. A method for using the functionalized choline chloride ionic liquid according to claim 1, comprising using the functionalized choline chloride ionic liquid as an electrolyte material or additive for an electrochemical energy storage device.

5. A method for using the functionalized choline chloride ionic liquid according to claim 1 as an electrolyte material or additive for an electrochemical energy storage device, comprising using the functionalized choline chloride ionic liquid as a quaternary ammonium salt-type ionic liquid electrolyte material, which is used as an electrolyte material or additive for an lithium-ion battery or supercapacitor.

* * * * *

UNITED STATES PATENT AND TRADEMARK OFFICE
CERTIFICATE OF CORRECTION

PATENT NO. : 9,728,806 B2
APPLICATION NO. : 14/648859
DATED : August 8, 2017
INVENTOR(S) : Lingzhi Zhang et al.

It is certified that error appears in the above-identified patent and that said Letters Patent is hereby corrected as shown below:

In the Specification

Column 8, Line 45, "Li/Li$^|$)," should read --Li/Li$^+$),--

Column 8, Line 47, "Li/Li$^|$)." should read --Li/Li$^+$).--

Signed and Sealed this
Fifth Day of December, 2017

Joseph Matal
*Performing the Functions and Duties of the*
*Under Secretary of Commerce for Intellectual Property and*
*Director of the United States Patent and Trademark Office*